US012590881B2

(12) United States Patent
Ma et al.

(10) Patent No.: US 12,590,881 B2
(45) Date of Patent: Mar. 31, 2026

(54) CELL SORTING CHIP, DEVICE AND METHOD BASED ON DIELECTROPHORESIS INDUCED DETERMINISTIC LATERAL DISPLACEMENT

(71) Applicant: QINGDAO INSTITUTE OF BIOENERGY AND BIOPROCESS TECHNOLOGY, CHINESE ACADEMY OF SCIENCE, Qingdao (CN)

(72) Inventors: Bo Ma, Qingdao (CN); Zhidian Diao, Qingdao (CN); Xixian Wang, Qingdao (CN); Jian Xu, Qingdao (CN)

(73) Assignee: QINGDAO INSTITUTE OF BIOENERGY AND BIOPROCESS TECHNOLOGY, CHINESE ACADEMY OF SCIENCE, Qingdao (CN)

( * ) Notice: Subject to any disclaimer, the term of this patent is extended or adjusted under 35 U.S.C. 154(b) by 720 days.

(21) Appl. No.: 17/994,176

(22) Filed: Nov. 25, 2022

(65) Prior Publication Data

US 2023/0266224 A1 Aug. 24, 2023

Related U.S. Application Data

(63) Continuation of application No. PCT/CN2021/096171, filed on May 26, 2021.

(30) Foreign Application Priority Data

May 26, 2020 (CN) .......................... 202010457651.9

(51) Int. Cl.
*G01N 15/1404* (2024.01)
*B01L 3/00* (2006.01)
(Continued)

(52) U.S. Cl.
CPC .... *G01N 15/1404* (2013.01); *B01L 3/502761* (2013.01); *C12N 1/16* (2013.01);
(Continued)

(58) Field of Classification Search
None
See application file for complete search history.

(56) References Cited

U.S. PATENT DOCUMENTS 6,749,736 B1 6/2004 Fuhr
2007/0125941 A1* 6/2007 Lee ........................ C12M 33/00
250/251
(Continued)

FOREIGN PATENT DOCUMENTS

CN 101745438 A 6/2010
CN 108587902 A 9/2018
(Continued)

OTHER PUBLICATIONS

Espacenet machine translation of CN 101745438 (Year: 2010).*
(Continued)

*Primary Examiner* — Elizabeth A Robinson
*Assistant Examiner* — Brittany I Fisher
(74) *Attorney, Agent, or Firm* — J.C. PATENTS

(57) ABSTRACT

Provided are a cell sorting chip, device, and method based on dielectrophoresis induced deterministic lateral displacement, the chip including a microfluidic channel (4), the microfluidic channel comprising a sample inlet (4.1), a straight channel, and two sample outlets; three groups of electrode array pairs are integrated at a bottom of the straight channel, the three electrode array pairs respectively being a focusing electrode group (1), a sorting electrode group (2), and a separating electrode group (3); the focusing electrode group is used for cell focusing and signal detection; the sorting electrode group is used for single cell sorting; and the
(Continued)

separating electrode group is used for single cell separation. High-speed, precise, and lossless target cell sorting can thus be implemented.

17 Claims, 3 Drawing Sheets

(51) Int. Cl.

| | |
|---|---|
| *C12M 1/00* | (2006.01) |
| *C12N 1/16* | (2026.01) |
| *C12N 1/20* | (2026.01) |
| *G01N 15/10* | (2024.01) |
| *G01N 15/149* | (2024.01) |

(52) U.S. Cl.
CPC ........ *C12N 1/20* (2013.01); *B01L 2200/0652* (2013.01); *B01L 2300/0645* (2013.01); *B01L 2300/0654* (2013.01); *B01L 2300/0864* (2013.01); *B01L 2400/0424* (2013.01); *B01L 2400/086* (2013.01); *G01N 2015/1422* (2013.01); *G01N 15/149* (2024.01)

(56) References Cited

U.S. PATENT DOCUMENTS

| | | | |
|---|---|---|---|
| 2012/0088295 A1 | 4/2012 | Yasuda | |
| 2013/0256197 A1* | 10/2013 | Katsumoto ............ | G01N 15/12 |
| | | | 209/127.1 |
| 2014/0262970 A1* | 9/2014 | Sato ........................ | B03C 5/005 |
| | | | 209/127.1 |
| 2015/0376692 A1* | 12/2015 | Esfandyarpour .... | G01N 27/745 |
| | | | 506/38 |
| 2019/0084011 A1 | 3/2019 | Imai | |

FOREIGN PATENT DOCUMENTS

| | | |
|---|---|---|
| CN | 109682745 A | 4/2019 |
| KR | 1020090083655 A | 8/2009 |
| WO | WO2012054904 A2 | 4/2012 |

OTHER PUBLICATIONS

International Search Report of PCT/CN2021/096171.
Written Opinion of PCT/CN2021/096171.
"The potential of a dielectrophoresis activated cell sorter (DACS) as a next generation cell sorter", Micro and Nano Syst Lett (2016) 4:2, pp. 1-10 for cells handling by dielectrophoresis, Microelectronic Engineering 87(2010).
A modular micro-fluidic platform 2124-2133.
First Office Action of the corresponding application EP21811971.7.
First Office Action of the corresponding application JP2022-572561.

* cited by examiner

CELL SORTING CHIP, DEVICE AND METHOD BASED ON DIELECTROPHORESIS INDUCED DETERMINISTIC LATERAL DISPLACEMENT

CROSS-REFERENCE TO RELATED APPLICATIONS

This application is a continuation application of international Application No. PCT/CN2021/096171, filed on May 26, 2021, which in turn claims the priority benefits of Chinese Patent Application No. 202010457651.9, filed on May 26, 2020. The contents of the above identified applications are incorporated herein by reference in their entirety.

TECHNICAL FIELD

The invention belongs to the field of biotechnology and instrument science, and particularly relates to a cell sorting chip, device and method based on dielectrophoresis induced deterministic lateral displacement.

BACKGROUND OF THE PRESENT INVENTION

The traditional biological characterization of biological cells is mainly based on the level of groups cells. However, the average measurement of heterogeneous groups depends on cell culture, the difference of single cells cannot be reflected, and most cells in nature are still difficult to culture. Functional identification and directional sorting of single cells do not depend on cell expansion, so that the step of cell culture can be skipped directly, and the heterogeneity of cells can be reflected. Fluorescence-activated cell sorting (FACS) is a high-throughput single-cell analysis technology, the application of which has greatly improved the identification efficiency of single cells. However, since most of cells have weak fluorescence effect or no fluorescence themselves, this method generally requires the addition of fluorescent labeling. In addition, in the identification of functional components in cell colonies, key cell phenotypes are often roughly known or completely unknown (i.e., "unknown" cell phenotypes), and there are no other biomarkers. It is exactly the purpose of these studies that is often to find these unknown but key phenotypes (and their biomarkers). Therefore, the bottleneck of "detecting unknown cell phenotypes" seriously limits the application of FACS and other cell sorting technologies in single cell research. Single-cell Raman spectroscopy (SCRS) is an efficient information identification technology of intracellular chemical substances, which can provide information on molecular composition and structure of intracellular compounds. Raman spectroscopy does not need any label when obtaining a chemical fingerprint spectrum of the whole single cell, so that it can identify the cell types, physiological characteristics and phenotypes changes of living cells, and can track and sort "unknown cell phenotypes" by using the changes of Raman signals of the cells. Flow-mode Raman-activated Cell Sorting (RACS) based on SCRS provides a new idea to solve the above bottleneck problems.

There are a series of Raman-activated cell sorting technologies in the prior art, such as optical tweezers, laser jet coupling, etc., which belong to the still versions of the Raman-activated cell sorting technologies. Although these systems are simple and practical, their throughput is too low, which hinders the application of the Raman spectroscopy in high-throughput sorting. In order to improve the throughput of single cell sorting, there has also been disclosed a Raman-activated droplet sorting system and method capable of achieving high-throughput sorting. However, this kind of solution uses water-in-oil droplets, which leads to a complicated flow path and poor operability, and fails fully meet the actual needs.

SUMMARY OF THE PRESENT INVENTION

Based on the above problems, the present application proposes a cell sorting chip, device and method based on dielectrophoresis induced deterministic lateral displacement, which realizes the effect of single cell sorting by applying a non-uniform electric field through a simple chip structure.

In order to achieve the above purpose, one aspect of the present application provides a cell sorting microfluidic chip based on dielectrophoresis induced deterministic lateral displacement, the microfluidic chip comprising a micro-channel, wherein the micro-channel comprises a sample inlet, a straight channel and two sample outlets; three groups of electrode array pairs are integrated at a bottom of the straight channel, the three groups of electrode array pairs respectively being a focusing electrode group, a sorting electrode group and a separation electrode group; the focusing electrode group is used for cell focusing and signal detection; the sorting electrode group is used for single cell sorting; and the separation electrode group is used for single cell separation.

The focusing electrode group and the separating electrode group comprise at least one pair of electrodes, and the sorting electrode group can be a pair of electrodes or be one electrode.

The focusing electrode group has at least one pair of electrode arrays, electrodes in each pair of electrode arrays are parallel to each other, one ends of electrodes in single electrode array are connected, the electrodes in each pair of electrode arrays are distributed in a spaced manner, and the electrodes have an included angle.

The electrodes have two sides, shape of which is similar to ">".

The included angle of the electrodes is a+b, and the range of electrode angles a and b is 0-90 degrees, preferably 15-45 degrees.

Where, a is an included angle between one side of the electrodes and a centerline, and b is an included angle between the other side of the electrodes and the centerline.

In one embodiment, the angles a and b are different.

In another embodiment, the angles a and b are the same.

The separation electrode group and the focusing electrode group have the same structure, but the included angles have different directions, and an included angle between electrode of the sorting electrode group and the centerline is a.

Shape of electrodes of the separation electrode group is similar to "<".

A width L of the pair of electrodes can be flexibly adjusted according to the width of the micro-channel.

A width D of the electrode and an electrode spacing d are adjustable according to the cell/particle size, but both the width D of the electrode and the electrode spacing d are larger than the maximum cell/particle size.

In another embodiment, the centerlines of electrode pairs of the focusing electrode group and the separating electrode group are not in the same straight line.

In another embodiment, a distance c between the center-lines of the electrode pairs of two groups is determined according to the electrode width D and the electrode spacing d.

In another embodiment, the width of the pair of electrodes L is 1 millimeter, the width of the electrode D is 25 microns, the distance between the electrodes d is 25 microns, the electrode angles a and b are both 30 degrees, and the distance c between the centerlines of the electrode pairs of the two groups is 35 microns.

In another embodiment, the electrode groups are made of conductive electrodes such as ITO, carbon, graphene or metal.

In another embodiment, a height of the electrode is 10 nanometers to 10 microns, preferably 50-150 nanometers.

In another embodiment, a material of a carrier of the electrode pair integrated at the bottom of the chip is silicate glass, quartz glass, calcium fluoride glass, PDMS (polydi-methylsiloxane) or PMMA (polymethyl methacrylate), pref-erably quartz glass.

In another embodiment, the groups of electrode array pairs are externally connected with a function generator for applying high-frequency alternating current to the elec-trodes.

In another embodiment, a response time of the sorting electrode group is 50 milliseconds.

By periodically applying high-frequency alternating cur-rent to the electrodes, the particles in the fluid flow along the electrodes. This is because by applying a non-uniform field, cells/particles in a solution which is not easily polarized will be subjected to a dielectrophoretic force perpendicular to and pointing to the electrode since the cells/particles are easily polarized, and at the same time, the cells will also be subjected to a fluid driving force parallel to and pointing to the flow direction, and the resultant force of the two forces move the cells along the electrode.

With respect to width of the straight channel, theoreti-cally, there is no upper limit for the width, and if the channel is wide, a good focusing effect can be achieved by increasing number of the electrode arrays.

In another embodiment, the width of the straight channel is 1-2 millimeters.

Another aspect of the present application provides a cell sorting device based on dielectrophoresis induced determin-istic lateral displacement, comprising:
a microfluidic chip;
a function generator for generating sinusoidal alternating current with different frequencies and voltages;
a computer for controlling the operation of a program and signal acquisition and collection of related optical instruments, controlling output voltage, frequency, duty ratio and other parameters of the function genera-tor, and controlling on/off of a relay;
the relay for controlling on/off of a circuit;
a fluid driving device serving as a driving force source for driving a fluid into the micro-channel.

In another embodiment, the fluid driving device com-prises an injection pump or a gravity driving device.

Yet another aspect of the present application provides a cell sorting method based on dielectrophoresis induced deterministic lateral displacement, specifically comprising the following steps:
1) cell sample injection: a fluid driving device is used to allow a fluid containing cells to enter a straight channel through a sample inlet of a microfluidic chip;
2) cell focusing: a focusing electrode group is connected with an output end of a function generator through a wire, and the cells in the fluid are focused to a signal monitoring point at an included angle of electrodes by periodically applying high-frequency voltage to the focusing electrode group;
3) signal detection: an optical signal acquisition point is aligned with the signal monitoring point 5 to perform optical signal detection, and a detected signal is pro-cessed by a computer program to judge whether it is a target cell or not;
4) cell sorting: when it is a target cell, a relay is triggered to communicate with the sorting electrode group to output high-frequency voltage, so that the target cell deviates from a centerline position along the sorting electrode group, when the program judges that it is a non-target cell, the program controls the relay not be turned on, to keep the non-target cell moving along original centerline position of the focusing electrode group without deviation;
5) cell separation: high-frequency voltage is periodically applied to the separation electrode group to allow the non-target cells and target cells in the fluid flow to different sample outlets.

In another embodiment, the cells are one or more of biological cells such as yeast cells, *Escherichia coli* cells, or *Hela* cells.

In another embodiment, a flow rate of the fluid is 0.01-50 microliters per minute, and the magnitude of the flow rate is related to the width and height of the straight channel, and the sample injection flow rate is preferably 10-40 microliters per minute.

Taking yeast as an example, yeast is washed with pure water for three times, and pure water is used as a sample injection buffer, with best parameters being electrification voltage of 16 volts and sinusoidal alternating current at a frequency of 10 MHz.

In another embodiment, duration of the applied high-frequency voltage is adjusted according to parameters such as the fluid flow rate in a flow field, and the loading time needs to meet the requirement of deviating the target cell by a distance greater than or equal to the distance c between centerlines of electrode pairs of the two groups.

The optical signal detection in step 3) is Raman signal detection or fluorescence signal detection.

There is a delay time between the optical signal detection in step 3) and the sorting in step 4), and the delay time is determined by the following calculation formula: Time interval=liquid flow length/liquid flow rate, wherein the liquid flow length refers to an actual distance through which the detected liquid flows from a signal monitoring point to a sorting operation point.

If the sorting electrode group and the separation electrode group are not triggered, the system method can be used as flow-mode cell detection, only performing signal detecting of each cell flowing through the detection point.

The invention has the beneficial effects that:
1) the chip micro-channel is simple in structure, and a flow path is a straight channel, which is simple and facilitates practical operation;
2) the response time of the sorting electrode is millisec-ond, so that the sorting efficiency with high throughput is achieved;
3) with the integration of the focusing electrode group, the cell sample injection flow rate can be greatly increased while the cell trap efficiency and detection efficiency are ensured, so that the cells are effectively prevented from settling in a sample injection microtube, the sample injection efficiency is improved, and the stable operation time of the system can be effectively prolonged.

DETAILED DESCRIPTION OF THE PRESENT INVENTION

The present application will be further explained in detail with reference to the attached drawings and embodiments below. It should be understood that these embodiments are for illustrative purposes only and are not intended to limit the scope of the present application.

Figures 1, 2:
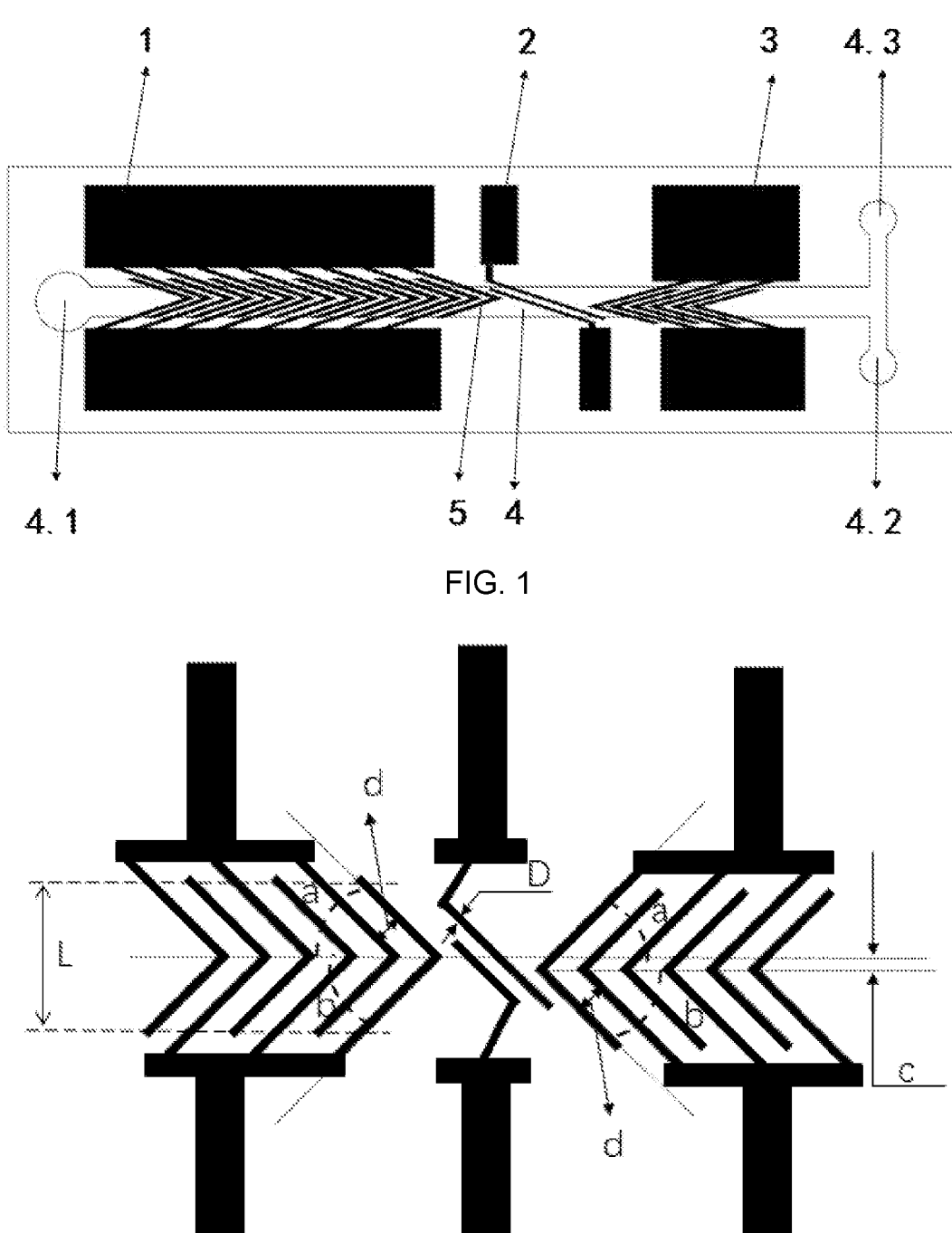
FIG. 1 is a schematic diagram of a cell sorting chip based on dielectrophoresis induced deterministic lateral displacement. Reference numerals: 1: focusing electrode group; 2: sorting electrode group; 3: separation electrode group; 4: micro-channel; 4.1: sample inlet; 4.2: collection port; 4.3: waste liquid port; 5: signal monitoring point.
FIG. 2 is a schematic diagram of various parameters of electrodes, in which a and b represent electrode included angles, d represents a distance between the electrodes, D represents a width of the electrode, c represents a distance between centerlines of electrode pairs of the two groups, and L represents a width of the pair of electrodes.

A structure of a microfluidic chip is as shown in FIG. 1. The microfluidic chip comprises a micro-channel 4, wherein the micro-channel comprises a sample inlet 4.1, a straight channel, a collection port 4.2 and a waste liquid port 4.3; three groups of electrode array pairs are integrated at a bottom of the micro-channel 4, the three groups of electrode array pairs respectively being a focusing electrode group 1, a sorting electrode group 2 and a separation electrode group 3; the focusing electrode group is used for cell focusing and signal detection; the sorting electrode group is used for single cell sorting; and the separation electrode group is used for single cell separation.

FIG. 2 is a schematic diagram of various parameters of electrodes, in which a and b represent electrode angles, d represents a distance between the electrodes, D represents a width of the electrode, c represents a distance between centerlines of electrode pairs of the two groups, and L represents a width of the electrode pairs.

Figure 3:
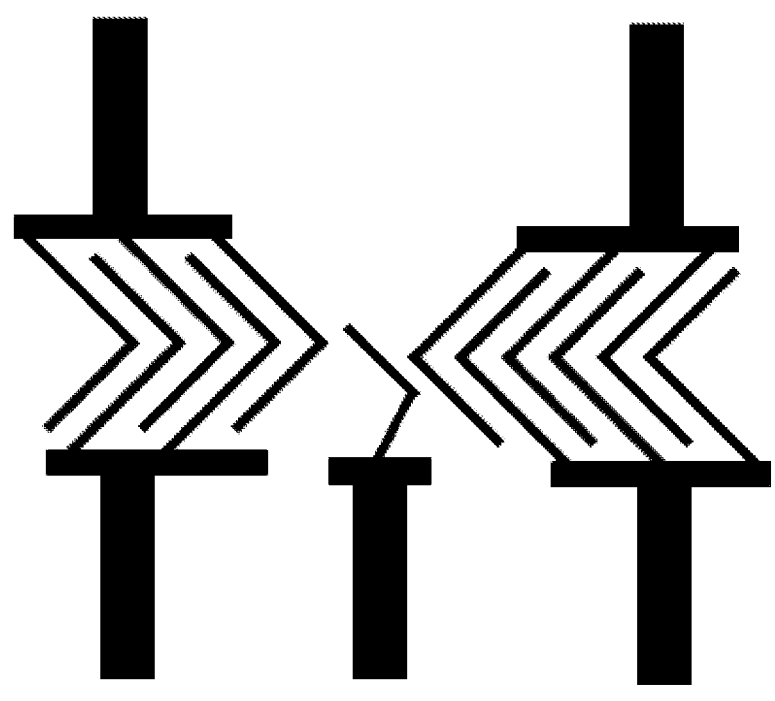
FIG. 3 is a schematic structural diagram of another electrode groups.

FIG. 3 is a schematic structural diagram of another electrode group. Wherein, the sorting electrode group has only one electrode.

Example 1: Flow-Mode Raman-Activated Cell Sorting of Yeast Cells with High Oil Yield Experiment Preparation:

One milliliter of cultured yeast cells is taken into a centrifuge tube and centrifuged for 5 minutes at 5000 rpm, a supernatant is removed, one milliliter of pure water is added for resuspension, and an obtained solution is centrifuged for 5 minutes at 5000 rpm; after washing for three times is performed, one milliliter of pure water is added for resuspension. According to the concentration of fungus, it is diluted by 1,000-10,000 times, a certain concentration of surfactant (such as PF127® with the final concentration of 0.5%) is added to prevent cells from adsorbing the electrode, and after mixing uniformly, the obtained solution is injected into a syringe.

A Raman instrument is turned on and a laser is turned on so that the laser is aligned with a signal monitoring point 5.

The structure of the adopted microfluidic chip is as shown in FIG. 3, and the parameters of the electrodes in the microfluidic chip are as follows: the width L of the electrode pair is 1 millimeter, the width D of the electrode is 25 microns, the distance d between the electrodes is 25 microns, the electrode angles a and b are both 30 degrees, and the distance c between the centerlines of the two groups of electrode pairs is 35 microns.

Figure 4:
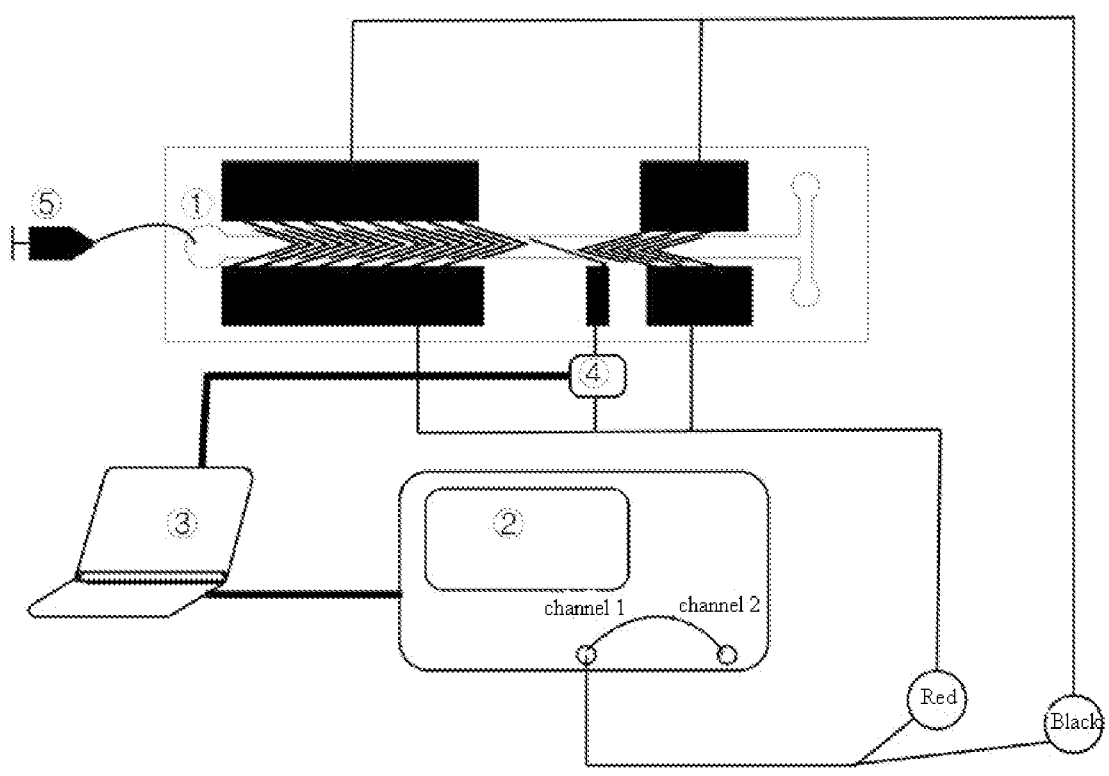
FIG. 4 is a schematic diagram of a cell sorting device based on dielectrophoresis induced deterministic lateral displacement. Reference numerals: ①: microfluidic chip; ②: function generator; ③: computer; ④: relay; ⑤: injection pump.
Figure 5:
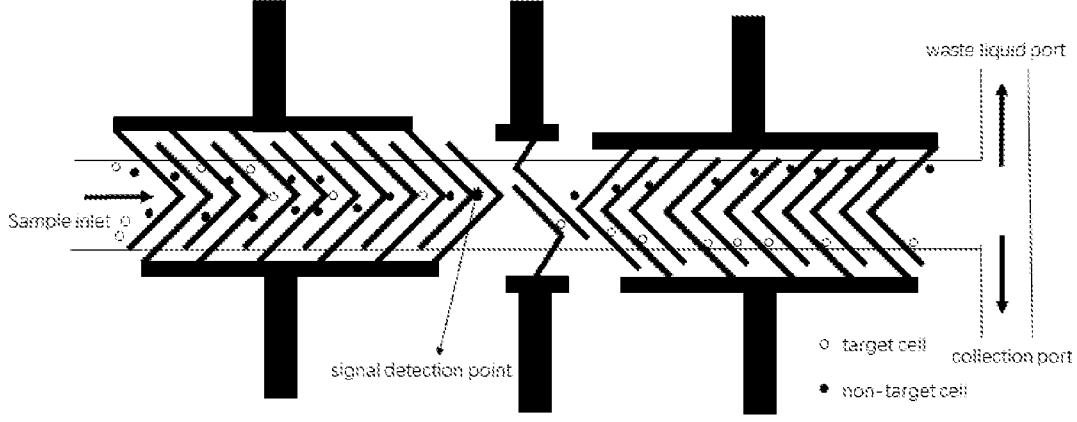
FIG. 5 is a schematic diagram of a cell sorting process based on dielectrophoresis induced deterministic lateral displacement.

A microfluidic chip ①, a function generator ②, a computer ③, a relay ④ and an injection pump ⑤ are connected as shown in FIG. 4, and a programmed program in the computer runs, so that an output channel 2 of the function generator controls an output channel 1, the channel 2 outputs a square wave with a voltage of 20 volts and a frequency of 5 Hz, and the channel 1 outputs a sine wave with a voltage of 16 volts and a frequency of 10 MHz. At the same time, the program controls the acquisition and analysis of a Raman signal, and when a target cell is detected, the program controls the conduction of the relay ④.

In the Experiment:

The above-mentioned treated fungus liquid is pumped into the micro-channel by the injection pump ⑤, and the yeast cells in the liquid gradually move to a tip of the electrode pair under the focusing action of the focusing electrode group, wherein a flow rate of the micro-channel is about 40 microliters per minute, the electrification parameter of the electrode is 16 volts, the frequency is 10 MHz, and the focusing trap efficiency reaches over 95%.

When the yeast cells move to the signal monitoring point, the Raman spectrum of them will be collected, and the program will simply analyze the collected spectrum. When it is a target cell, the Raman spectrum reflects a characteristic peak of oil, so that the program judges that it is the target cell, and the program controls the relay to be activated to allow the sorting electrode group to be turned on, and with the durations of delay and loading being set in advance, the target cell moves downwards; when it is a non-target cell, the Raman spectrum will not show the characteristic peak of oil, so that the relay will not be activated, the sorting electrode group thus has no voltage loading, and the cell continues to move along the centerline.

The function of the separation electrode group is to allow the cells at both ends of the centerline of the separation electrode group to deviate from the centerline further, so that the target cells are below the channel and the non-target cells are above the channel.

Finally, yeast cells with high oil yield are collected at the collection port, and yeast cells with low oil yield or no oil yield are collected at the waste liquid port.

End of Experiment:

The microfluidic chip channel is rinsed with absolute ethanol twice, and then put in an oven for drying and recycling.

Example 2: Flow-Mode Raman-Activated Cell Detection of Yeast Cells with High Oil Yield Experiment Preparation:

One milliliter of cultured yeast cells is taken into a centrifuge tube and centrifuged for 5 minutes at 5000 rpm, a supernatant is removed, one milliliter of pure water is added for resuspension, and an obtained solution is centrifuged for 5 minutes at 5000 rpm; after washing for three times is performed, one milliliter of pure water is added for resuspension. According to the concentration of fungus, it is diluted by 1,000-10,000 times, a certain concentration of surfactant (such as PF127® with the final concentration of 0.5%) is added to prevent cells from adsorbing the electrode, and after mixing uniformly, the obtained solution is injected into a syringe.

A Raman instrument is turned on and a laser is turned on so that the laser is aligned with a signal monitoring point 5.

The structure of the adopted microfluidic chip is as shown in FIG. 3, and the parameters of the electrodes in the microfluidic chip are as follows: the width L of the electrode pair is 1 millimeter, the width D of the electrode is 25 microns, the distance d between the electrodes is 25 microns, the electrode angles a and b are both 30 degrees, and the distance c between the centerlines of the two groups of electrode pairs is 35 microns.

A microfluidic chip ①, a function generator ②, a computer ③, a relay ④ and an injection pump ⑤ are connected as shown in FIG. 4, and a programmed program in the computer runs, so that an output channel 2 of the function generator controls an output channel 1, the channel 2 outputs a square wave with a voltage of 20 volts and a frequency of 5 Hz, and the channel 1 outputs a sine wave with a voltage of 16 volts and a frequency of 10 MHz. At the same time, the program controls the acquisition and analysis of a Raman signal.

The above-mentioned treated fungus liquid is pumped into the micro-channel by the injection pump ⑤, and the yeast cells in the liquid gradually move to a tip of the electrode pair under the focusing action of the focusing electrode group, wherein a flow rate of the micro-channel is about 40 microliters per minute, the electrification parameter of the electrode is 16 volts, the frequency is 10 MHz, and the focusing trap efficiency reaches over 95%.

When yeast cells move to the signal monitoring point, the Raman spectrum of them will be collected, and the program will simply analyze the collected spectrum.

Finally, yeast cells after being detected are collected at the collection port.

End of Experiment:

The microfluidic chip channel is rinsed with absolute ethanol twice, and then put in an oven for drying and recycling.

By analyzing the collected Raman spectra later, relevant information such as the proportion of yeast cells with high oil yield can be obtained.

Example 3: Flow-Mode Sorting of Fluorescent Cells

Experiment Preparation:

One milliliter of cultured *Escherichia coli* capable of expressing fluorescent protein is taken into a centrifuge tube and centrifuged for 5 minutes at 5000 rpm, a supernatant is removed, one milliliter of pure water is added for resuspension, and an obtained solution is centrifuged for 5 minutes at 5000 rpm; after washing for three times is performed, one milliliter of pure water is added for resuspension. According to the concentration of fungus, it is diluted by 1,000-10,000 times, a certain concentration of surfactant (such as PF127® with the final concentration of 0.5%) is added to prevent cells from adsorbing the electrode, and after mixing uniformly, the obtained solution is injected into a syringe.

A fluorescence imaging instrument is turned on and a laser is turned on so that the laser is aligned with a signal monitoring point 5.

A structure of the adopted microfluidic chip is as shown in FIG. 3, wherein the width L of the electrode pair is 1 millimeter, the width D of the electrode is 25 microns, the distance d between the electrodes is 25 microns, the electrode angles a and b are both 15 degrees, and the distance c between the centerlines of the two groups of electrode pairs is 50 microns.

A microfluidic chip ①, a function generator ②, a computer ③, a relay ④ and an injection pump ⑤ are connected as shown in FIG. 4, and a programmed program in the computer runs, so that an output channel 2 of the function generator controls an output channel 1, the channel 2 outputs a square wave with a voltage of 20 volts and a frequency of 0.2 Hz, and the channel 1 outputs a sine wave with a voltage of 16 volts and a frequency of 1 MHz. At the same time, the program controls the acquisition and analysis of a fluorescence signal, and when a target cell is detected, the program controls the relay ④ to be turned on.

In the Experiment:

The above-mentioned treated bacteria liquid is pumped into the micro-channel by the injection pump ⑤, and the *Escherichia coli* cells in the liquid gradually move to a tip of the electrode pair under the focusing action of the focusing electrode group, wherein a flow rate of the micro-channel is about 10 microliters per minute, the electrification parameter of the electrode is 16 volts, the frequency is 1 MHz, and the focusing trap efficiency reaches over 90%.

When *Escherichia coli* cells move to the signal monitoring point, the *Escherichia coli* containing fluorescent protein is excited by the laser to emit a fluorescent signal that is collected by the computer, the program controls the relay to be activated to allow the sorting electrode group to be turned on, and with the durations of delay and loading being set in advance, the target cell deviates downwards; when the *Escherichia coli* without the fluorescent protein passes through the monitoring point, the fluorescent signal will not be excited, so that the program controls the relay not to be activated, the sorting electrode group has no voltage loading, and the cell continues to move along the centerline.

The function of the separation electrode group is to allow the cells at both ends of the centerline of the separation electrode group to deviate from the centerline further, so that the target cells are below the channel and the non-target cells are above the channel.

Finally, *Escherichia coli* with fluorescence is collected at the collection port, and non-fluorescent *Escherichia coli* cells are collected at the waste liquid port.

End of Experiment:

The microfluidic chip channel is rinsed with absolute ethanol twice, and then put in an oven for drying and recycling.

It will be appreciated that various alterations and modifications of the invention will become apparent to those skilled in the art after having read the above teachings of the invention, and that such equivalents are intended to fall within the scope of the invention as defined in the appended claims.

The invention claimed is:

1. A cell sorting microfluidic chip based on dielectrophoresis induced deterministic lateral displacement, comprising a micro-channel, wherein the micro-channel comprises a sample inlet, a straight channel and two sample outlets; three groups of electrode array pairs are integrated at a bottom of the straight channel, the three groups of electrode array pairs respectively being a focusing electrode group, a sorting electrode group and a separation electrode group; the focusing electrode group is used for cell focusing and signal detection; the sorting electrode group is used for single cell sorting; and the separation electrode group is used for single cell separation; wherein:

the focusing electrode group comprises one or more electrode pairs, the separation electrode group comprises one or more electrode pairs, and the sorting electrode group comprises at least one electrode;

each electrode in the one or more electrode pairs of the focusing electrode group has two first arms connected at a first tip point, a first centerline of the focusing electrode group passes the first tip point of each electrode in the one or more electrode pairs, an included angle between one of the two first arms and the first centerline has a value a, an included angle between the other one of the two first arms and the first centerline has a value b, an included angle between the two first arms of each electrode has a value a+b;

the two first arms of different electrodes in the one or more electrode pairs of the focusing electrode group are parallel to each other, relatively, and the electrodes in the one or more electrode pairs of the focusing electrode group are distributed in a spaced manner;

each electrode in the one or more electrode pairs of the separation electrode group has two second arms connected at a second tip point, a second centerline of the separation electrode group passes the second tip point of each electrode in the one or more electrode pairs, an included angle between one of the two second arms and the second centerline has a value a, an included angle between the other one of the two second arms and the second centerline has a value b, an included angle between the two second arms of each electrode has a value a+b;

each electrode in the one or more electrode pairs of the separation electrode group and each electrode in the one or more electrode pairs of the focusing electrode group have a same structure, while the included angle between the two first arms of each electrode in the one or more electrode pairs of the focusing electrode group and the included angle between the two second arms of each electrode in the one or more electrode pairs of the separation electrode group are of different directions; and the at least one electrode of the sorting electrode group has a third arm, and an included angle between the third arm and the first centerline of the focusing electrode group has a value a.

2. The microfluidic chip according to claim 1, wherein the value a and b are in the range of 15-45 degrees, respectively.

3. The microfluidic chip according to claim 2, wherein the value a and b are the same.

4. The microfluidic chip according to claim 1, wherein the first centerline of the focusing electrode group and the second centerline of the separating electrode group are not in a same straight line.

5. The microfluidic chip according to claim 1, wherein the focusing electrode group, the sorting electrode group and the separation electrode group are made of ITO, carbon, graphene, or metal.

6. The microfluidic chip according to claim 1, wherein the first centerline of the focusing electrode group and the second centerline of the separating electrode group are parallel to each other with a distance c therebetween.

7. The microfluidic chip according to claim 6, wherein the distance c is in the range of 35-50 microns.

8. The microfluidic chip according to claim 1, wherein the focusing electrode group, the sorting electrode group and the separation electrode group are arranged in sequence; each electrode in the one or more electrode pairs of the focusing electrode group is of a ">" shape, and each electrode in the one or more electrode pairs of the separation electrode group is of a "<" shape.

9. The microfluidic chip according to claim 8, wherein the first centerline of the focusing electrode group and the second centerline of the separating electrode group are not in a same straight line.

10. The microfluidic chip according to claim 8, wherein the first centerline of the focusing electrode group and the second centerline of the separating electrode group are parallel to each other with a distance c therebetween.

11. A cell sorting device based on dielectrophoresis induced deterministic lateral displacement, comprising:

the microfluidic chip of claim 1;

a function generator, for generating sinusoidal alternating current with different frequencies and voltages;

a computer, for controlling operation of a program and signal acquisition and collection of optical instruments, controlling output voltage, frequency, duty ratio of the function generator, and controlling on/off of a relay;

the relay, for controlling on/off of a circuit;

a fluid driving device, serving as a driving force source for driving a fluid into the micro-channel.

12. The cell sorting device based on dielectrophoresis induced deterministic lateral displacement according to claim 11, wherein the fluid driving device comprises an injection pump or a gravity driving device.

13. A cell sorting method based on dielectrophoresis induced deterministic lateral displacement, which adopts the cell sorting device of claim 11, comprising the following steps:

1) Cell sample injection: the fluid driving device is used to allow the fluid containing cells to enter the straight channel through the sample inlet of the microfluidic chip;

2) cell focusing: the focusing electrode group is connected with an output end of the function generator through a wire, and the cells in the fluid are focused to a signal monitoring point at the included angle between the two first arms by periodically applying high-frequency voltage to the focusing electrode group;

3) signal detection: an optical signal acquisition point is aligned with the signal monitoring point to perform optical signal detection, and a detected signal is processed by the program to judge whether it is a target cell or not;

4) Cell sorting: when it is a target cell, the relay is triggered to communicate with the sorting electrode group to output high-frequency voltage, so that the target cell deviates from the first centerline of the focusing electrode group along the sorting electrode group, when the program judges that it is a non-target cell, the program controls the relay not be turned on, to keep the non-target cell moving along the first center-line of the focusing electrode group without deviation;

5) Cell separation: high-frequency voltage is periodically applied to the separation electrode group to allow the non-target cells and the target cells in the fluid flow to different sample outlets.

14. A cell sorting method based on dielectrophoresis induced deterministic lateral displacement, which adopts microfluidic chip of claim 1, comprising the following steps:

1) Cell sample injection: a fluid driving device is used to allow a fluid containing cells to enter the straight channel through the sample inlet of the microfluidic chip;

2) cell focusing: the focusing electrode group is connected with an output end of a function generator through a wire, and the cells in the fluid are focused to a signal monitoring point at the included angle between the two first arms by periodically applying high-frequency voltage to the focusing electrode group;

3) signal detection: an optical signal acquisition point is aligned with the signal monitoring point to perform optical signal detection, and a detected signal is processed by a computer program to judge whether it is a target cell or not;

4) Cell sorting: when it is a target cell, a relay is triggered to communicate with the sorting electrode group to output high-frequency voltage, so that the target cell deviates from the first centerline of the focusing electrode group along the sorting electrode group; when the program judges that it is a non-target cell, the program controls the relay not be turned on, to keep the non-target cell moving along the first centerline of the focusing electrode group without deviation;

5) Cell separation: high-frequency voltage is periodically applied to the separation electrode group to allow the non-target cells and the target cells in the fluid flow to different sample outlets.

15. The cell sorting method based on dielectrophoresis induced deterministic lateral displacement according to claim 14, wherein the cells are yeast cells, *Escherichia coli* cells, or *Hela* cells.

16. The cell sorting method based on dielectrophoresis induced deterministic lateral displacement according to claim 14, wherein a flow rate of the fluid is 0.01-50 microliters per minute.

17. The cell sorting method based on dielectrophoresis induced deterministic lateral displacement according to claim 14, wherein the optical signal detection in step 3) is Raman signal detection or fluorescence signal detection.

* * * * *